United States Patent [19]
DeGiorgi et al.

[11] Patent Number: 5,905,204
[45] Date of Patent: May 18, 1999

[54] TEST SPECIMEN DESIGN INCORPORATING MULTIPLE FRACTURE SITES AND MULTIPLE STRAIN MATERIAL FRACTURES

[75] Inventors: Virginia G. DeGiorgi, Nanjemoy, Md.; Andrew B. Geltmacher, Alexandria, Va.

[73] Assignee: The United States of America as represented by the Secretary of the Navy, Washington, D.C.

[21] Appl. No.: 09/040,376

[22] Filed: Mar. 18, 1998

Related U.S. Application Data

[62] Division of application No. 08/845,848, Apr. 28, 1997.

[51] Int. Cl.$^6$ ........................................................ G01N 3/08
[52] U.S. Cl. .................................................. 73/826; 73/804
[58] Field of Search ................................ 73/788, 789, 799, 73/804, 826

[56] References Cited

U.S. PATENT DOCUMENTS

| | | | |
|---|---|---|---|
| 5,022,272 | 6/1991 | Bronowicki et al. | 73/772 |
| 5,431,060 | 7/1995 | Lauren | 73/826 |
| 5,508,801 | 4/1996 | Panin et al. | 356/35.5 |
| 5,581,040 | 12/1996 | Lin | 73/833 |

*Primary Examiner*—Max H. Noori
*Attorney, Agent, or Firm*—Thomas E. McDonnell; Charles J. Stockstill

[57] ABSTRACT

A material test specimen design is taught for the determination of critical strain and stress states for multiaxial fracture. The objective of the specimen is to increase the amount of data obtained per specimen while retaining simplicity in testing procedure by using standard tension testing machines to generate the primary deformation of the specimen. The specimen, in conjunction with analytical or computational simulation, uses nonuniform deformation fields produced by secondary and tertiary strain concentrations to generate and track these multiaxial strain states to fracture. Typically, the primary deformation is uniaxial tension of a panel, the secondary strain concentration is a circular hole in the panel and the tertiary strain concentrations are areas of reduced thickness within the deformation field of the circular hole. Multiaxial strain ratios from −0.50 to −0.10 and control over fracture initiation sites may be generated by a test specimen design of the type taught by this invention.

3 Claims, 7 Drawing Sheets

TEST SPECIMEN DESIGN INCORPORATING MULTIPLE FRACTURE SITES AND MULTIPLE STRAIN MATERIAL FRACTURES

This application is a Division of application Ser. No. 08/845,848 filed Apr. 28, 1997.

BACKGROUND OF THE INVENTION

1. Field of the Invention

This invention pertains generally to a material test specimen for conducting stress and strain measurements and more specifically to a test specimen tailored to provide information on multiaxial stress and strain states in a controlled manner under tensile deformation.

2. Description of the Related Art

Identification of the fracture limit surface for multiaxial strain states, as shown in FIG. 1, is needed for manufacturing process design, structural design and structural integrity prediction. This is particularly true for strain-path-dependent fracture in metal alloys. Current practice in multiaxial strain state fracture limit diagrams is based on two existing methods for determining material mechanical behavior under multiaxial stress states; "tension-torsion-internal pressure" testing apparatus and the "hydrostatic bulge" testing apparatus. The material specimens are either hollow cylindrical tubes of uniform wall thickness or sheet specimens of uniform thickness, respectively. Both of these specialized test procedures are effective but require specialized test equipment which is generally specifically designed and dedicated to the purpose of multiaxial material characterization and testing. Both procedures have a low "data yield" per specimen, producing one strain history and one fracture datum point per specimen. Both test procedures also strive to preserve homogenous deformation fields for their ease of data reduction that such direct measurement allows. Determining a complete fracture limit diagram for multiple stress states requires many individual tests and is time consuming and expensive.

This invention teaches a new material test specimen geometry, wherein, the geometry features commonly referred to as "stress concentrators" generate stress and strain gradients in the material under test, supplemented by computational simulation of the test specimen.

The computational simulation of material test specimens, as a means of using nonuniform material deformation fields, has been used by K. S. Pister, Constitutive Modeling and Numerical Solution of Field Problems, Nuc. Engng. Design, Vol. 28, pp. 137–146, 1974; Idling et al., Identification of Nonlinear Elastic Solids by a Finite Element Method, Comp. Meth. Appl. Mech. Engng., Vol. 4, pp. 121–142, 1974; Norris et al., A Computer Simulation of the Tension Test, J. Mech. Phys. Solids, Vol. 26, pp. 1–19, 1978; and Matic et al., The Relationship of Tensile Specimen Size and Geometry Effects to Unique Constitutive Parameters for Ductile Materials, Proc. Royal Soc. Lond., Vol. A417, pp. 309–333, 1988; for nonlinear elastic and elastic-plastic constitutive parameter determination.

SUMMARY OF THE INVENTION

The object of this invention is to speed and ease the determination of fracture limits of metallic materials at various stress and strain states.

This and other objectives are accomplished by using a new design for a test specimen. This specimen is tailored to provide information on multiaxial stress and strain states in a controlled manner under tensile deformation by employing any commonly available tension testing apparatus, and stress analysis using appropriate and commonly available analytical methods or computer software. The specimen is also designed to provide information for more than one stress and strain state from a single specimen, if desired.

DESCRIPTION OF THE PREFERRED EMBODIMENT

This invention seeks to increase the data yield from a single material test specimen (FIG. 2a), tested in a standard uniaxial tension test machine, by producing more than one multiaxial strain state (and associated stress state) per specimen. The multiaxial strain and stress states may be characterized by their principle strain and stress ratios. This relaxes the traditional requirement that the specimen deformation be uniform, since multiple multiaxial strain states per specimen explicitly requires nonuniform deformation. In place of the uniform deformation requirement, this invention supplements the physical test data by computational simulation of the test specimen which requires that an appropriate constitutive model and parameters for the material are known and that the objective of the test is the fracture limit surface.

To accomplish this, this invention teaches a new material test specimen geometry which employs combinations of what are commonly called "stress concentrators" that generate stress and strain gradients in the material under test. The material test specimen geometry can be considered a combination of several geometric features. The test specimen geometry is composed of three basic geometric features: first, a primary outer geometry suitable for the tension test machine which generates a global deformation field (FIG. 2a); secondly, a secondary inner geometry that produces nonuniform deformation from the global deformation (FIG. 2b) and lastly, a set of tertiary inner geometries that modulate the nonuniform deformation to promote or avoid fracture at various strain and stress states as desired (FIG. 2c or 2d).

Figure 1:
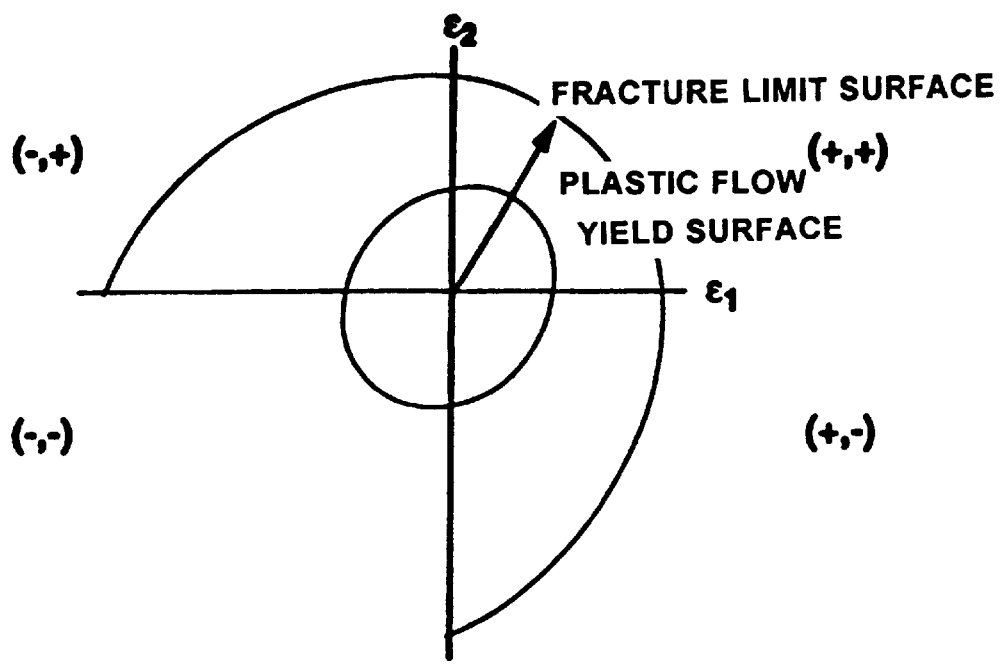
FIG. 1 shows a diagram of principal strain fracture limit surface.
Figure 2:
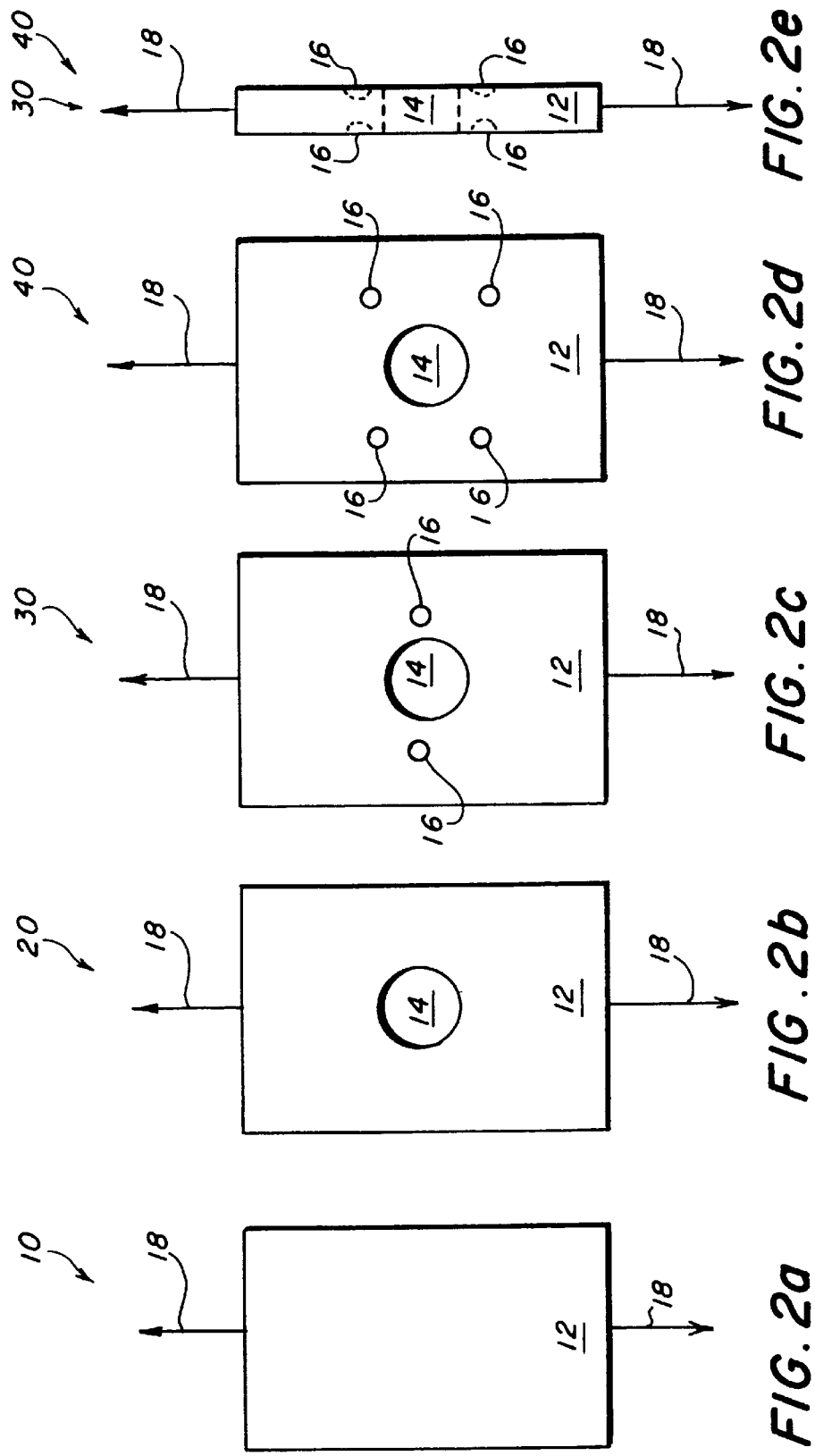
FIG. 2a shows a schematic of a typical uniaxial tension test specimen.
FIG. 2b shows a test specimen having a primary uniaxial geometry and a secondary geometry of a through-thickness hole which generates a global multiaxial deformation field.
FIG. 2c shows a test specimen having tertiary inner geometries at 0° and 180° of reduced thickness that produces nonuniform deformation from the global uniaxial loading.
FIG. 2d shows an alternative test specimen having a set of tertiary inner geometries that modulate the nonuniform deformation to promote or avoid fracture at various strain at, for example 45°, 135°, 225°, and 315°, and stress states as desired.
FIG. 2e shows a side view of a test specimen (FIG. 2d) having a set of tertiary inner geometries that modulate the nonuniform deformation to promote or avoid fracture at various strain and stress states as desired and an area of reduced thickness.

In the preferred embodiment 10, as shown in FIGS. 2, the primary geometry of the test specimen, for example, begins with a standard 0.063 inch thick tension test specimen 12, comparable in principle to the ASTM E-8 tension specimen. The width, for purposes of the example, is selected to be 2.0 inches. This facilitates testing in a standard tension test machine by appropriate gripping at each end of the specimen 12. Such use of standard geometry and loading produces a primary tension deformation field which is nominally uniform. To conduct the testing, an Instron hydraulic test machine with hydraulic grips (not shown) may be used, or any other test machine capable of performing the same function, i.e., testing the specimen in tension.

A broad range of multiaxial stress and strain states are generated by the introduction of a circular through-thickness hole 14 as the secondary geometry. The hole 14, preferably one quarter of the specimen width, for example, is 0.50 inches in diameter, is positioned at the center of the specimen 12. A broad range of multiaxial strain and stress states are generated around the hole 14 upon loading of the test specimen 12. The maximum stress and strain components are found at the edge of the hole 12 on the diameter, perpendicular to the tension axis of the specimen 12. For illustration, this diameter will be referred to as the 000–180 degree directions (or simply the 000 direction to indicate equivalent directions). The loading direction 18 lies along the 090–270 degree directions. The specimen is deformed (extended under tension) in a controlled fashion in a test fixture. The test specimen is monitored (observed, photographed, video taped, or otherwise instrumented) to identify when and where fracture occurs. The force versus extension response of the specimen is recorded on a memory device, such as a computer disk. Fracture will normally occur at these two equivalent points. The stress free boundary produces a uniaxial state of stress, so fracture at these locations measures this one state of stress if only the primary and secondary geometries were included in the specimen 12 design.

The key to increasing the data yield from the specimen 12 is the ability to generate fracture sites away from the specimen 12 and secondary 14 boundaries and to increase the number of fracture sites. Hence, a qualitative and quantitative change in traditional specimen responses is desired. This requires raising the magnitudes of multiaxial strain and stress states located at points interior to the boundary of the specimen 12.

Figure 5A:
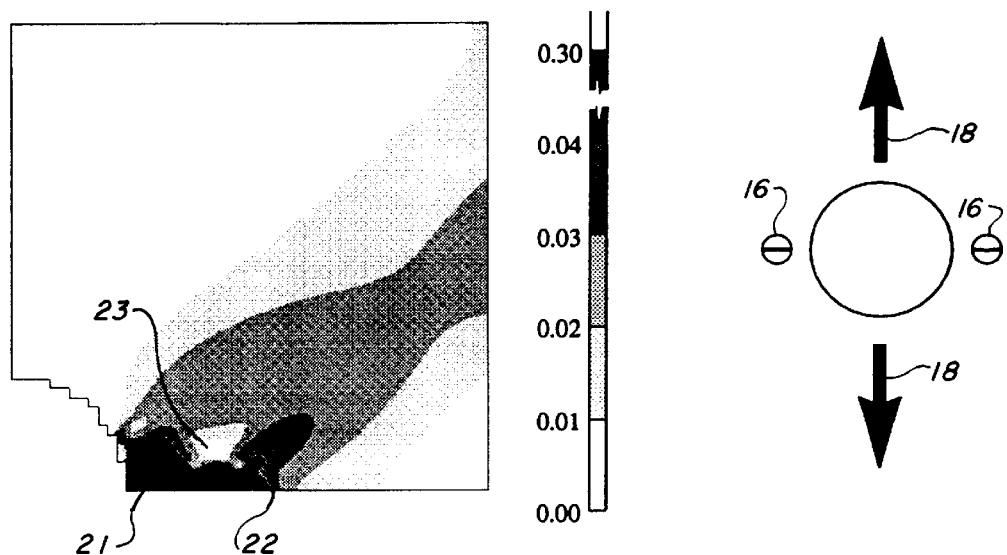
FIG. 5a shows the predicted equivalent plastic strain in a tension specimen with through-thickness hole and reduced thickness ratio of 0.33 at 0 and 180 degrees (FIG. 2c).
Figure 5B:
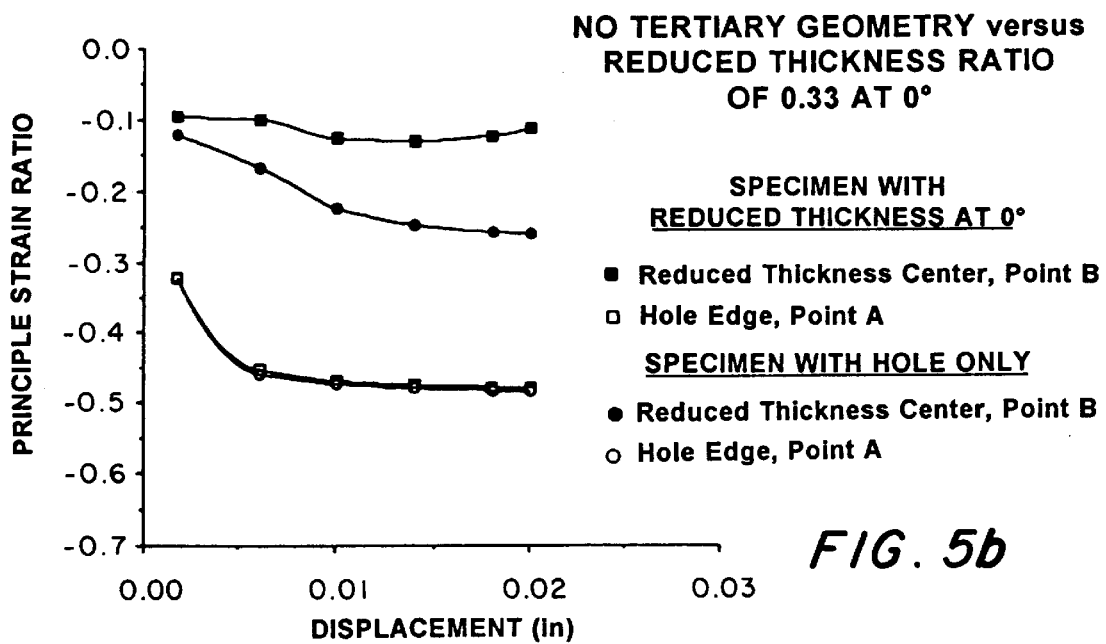
FIG. 5b shows a predicted principal strain ratio vs. global displacement history for a specimen in tension with a hole and reduced thickness ratio of 0.33 at 0 and 180 degrees (FIG. 2c) compared to specimen with no tertiary geometry (FIG. 2b).
Figure 5C:
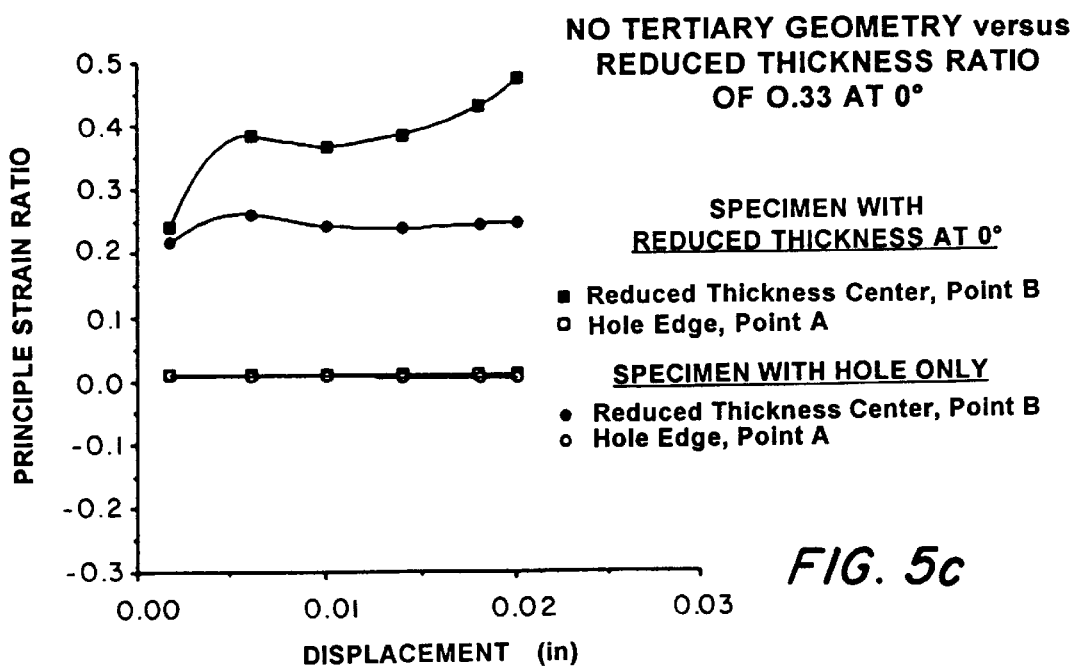
FIG. 5c shows a predicted principal stress ratio vs. global displacement history for a specimen in tension with a hole and reduced thickness ratio of 0.33 at 0 and 180 degrees (FIG. 2c) compared with no tertiary geometry (FIG. 2b).

The magnitudes of multiaxial strain and stress states are increased by introducing the tertiary geometric features 16, as shown in FIG. 2c, and upon applying a global tension deformation will generate local multi-axial strain states, as shown in FIGS. 5a–c. Tertiary deformation concentration geometry features, such as areas of reduced thickness 16 as shown in FIGS. 2c, 2d and 2e, may be used. Specimen 12 symmetry, with respect to both the loading axis and the 000–180 degree diameter, was preserved by reducing the thickness at equivalent multiple sites as necessary. A truncated spherical profile, on both sides of the specimen 12, can be generated using a spherical ball mill (not shown). This reduced thickness 16 will be characterized by the ratio of the minimum thickness to the sheet thickness. Points 21, 22, and 23, which are subsequently plotted for comparison of hole 14 edge and reduced section strains and stresses, are noted in FIG. 3.

After a test, a stress analysis is performed utilizing appropriate analytical or computational simulation to recreate the stress and strain histories throughout the specimen. It is assumed that the material response, generally characterized by a constitutive model and constitutive parameters, are known through a separate set of standard tests which do not produce the fracture limits of the material. Correlation between the physically observed event fracture and the calculated stress and strain states are used to establish the fracture limits. In practice, the precise position of the geometric features of the specimen would be selected to highlight strain states of interest motivated by or identified through some other design or manufacturing activity requiring knowledge of the fracture limits of the selected material.

The specimen model 12, consistent with the sheet thickness, for instance, was initially composed of 2500 8-noded plane stress elements, minus 112 elements removed to create the hole 14, for a final model size of 2388 elements. The nodes on the x-axis are constrained in the y-direction and the nodes on the y-axis are constrained in the x-direction, consistent with the model symmetry about these axes. The global displacement is applied to the top row of nodes in the positive y-direction.

Experimental Test

In an experimental test, a test specimen of 2024 aluminum sheet in the T3 condition having a width of 2 inches and a thickness of 0.063 inches was utilized and tested to failure in standard tension testing machine (1332 Instron Testing Machine or Model 810 MTS Testing Machine). The test specimen geometry was used in conjunction with the isotropic incremental elastic-plastic material model in ABAQUS/Standard finite element software of Hibbitt, Karlsson and Sorensen (HKS), Inc., of Pawtucket, R.I. The yield stress of this alloy is nominally 50.0 ksi. Nonlinear strain hardening proceeds to a true stress of 85.1 ksi at a log plastic strain of 0.151. The finite element models were run on a Cray YMP-EL computer. Data was post processed using Patran P3, Version 1.2, Mac-Neal Schwendler Corporation, Los Angeles, Calif. and ABAQUS/Abapost, HKS, Inc.

In the experimental results for the first specimen tested i.e., the benchmark tension specimen with a hole and no reduced thickness 16 sections, fracture initiated at the 000 and 180 degree locations on the surface of the hole.

Figure 3:
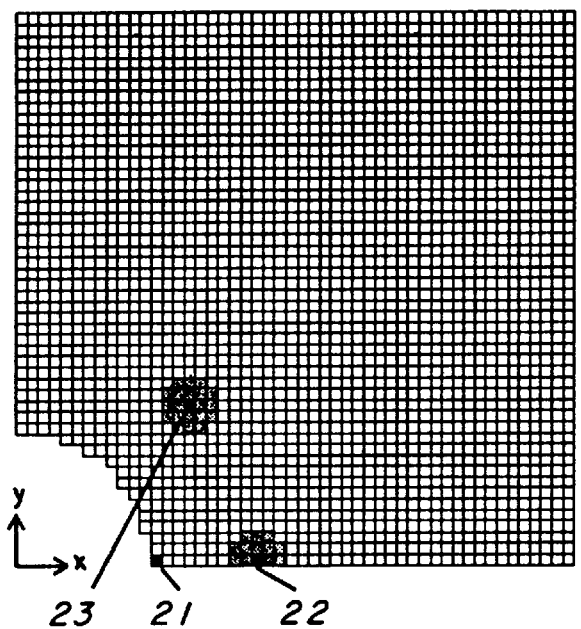
FIG. 3 depicts a finite element model mesh showing the locations of reduced thickness sections, and points at hole edge and reduced thickness sections used to plot stress and strain ratio histories.
Figure 4:
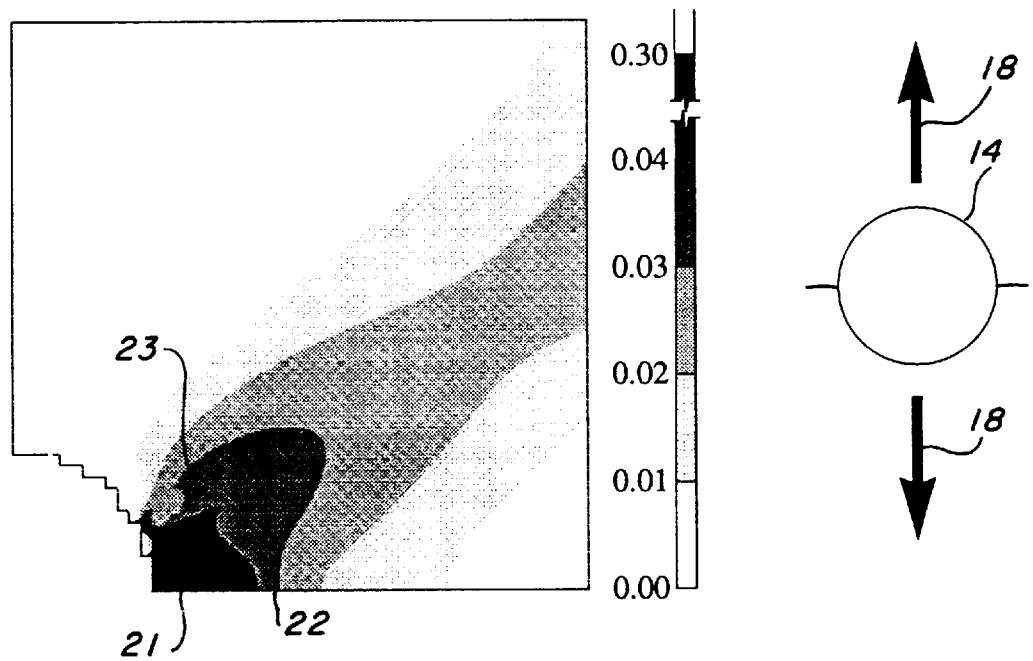
FIG. 4 shows the predicted equivalent plastic strain in a tension specimen with through-thickness hole but without reduced thickness areas (FIG. 2b).

Discussion of the results of all finite element analyses is in terms of the equivalent plastic strain contours, the principal in-plane strain ratio histories and the principal in-plane stress ratio histories. The equivalent plastic strain distribution for the secondary specimen 20 is shown in FIG. 4. The region influenced by the hole is clearly evident in the specimen without the reduced sections. The approximation to the circular shaped hole in the model moved the highest predicted stress and strain concentration from Point 21, as shown in FIG. 3, which is the physically correct position for the actual hole, to points on the hole edge slightly off the horizontal axis. This is not a major factor in interpreting the results on strain ratios at the hole edge, although the magnitudes of the strain and stress fields are somewhat different.

The size and shape of the equivalent plastic strain region in the secondary specimen 20 is used to guide the placement of the reduced thickness 16 sections of the tertiary specimens 30 and 40. The position of the 0.04 equivalent plastic strain contour, in particular, is used for positioning the reduced thickness 16 section at the 000–180 degree positions of the x-axis. An imaginary circle of radius 0.44 inches, 1.75 times that of the circular hole radius, is placed on the specimens and the reduced thickness 16 sections placed at the 000–180 degree positions. The same radius is used for the third and fourth specimen geometries with reduced sections at the 045-135-225-315 degree positions, respectively, for the remaining specimens with the goal of inducing failure at these locations rather than at the hole periphery.

The results of a test with a tertiary specimen 30, with the reduced thickness sections 16 at 000–180 degrees, showed successful initiation of fracture in both reduced thickness 16 sections. The finite element prediction of the equivalent plastic strain field is shown in FIG. 5a. The analysis shows that the magnitude of the deformation has been increased in the vicinity of the reduced thickness 16 section to a sufficient degree, in combination with changes in strain state, to produce fracture at this point. Comparison of Point 21, at the hole boundary, and Point 22, at the reduced section, shows principal strain ratios of −0.50 and −0.10, respectively (FIG. 5b) and principal stress ratios of 0.00 and 0.50 (FIG. 5c), respectively, in the plastic region. It is noted that the strain ratios at the hole edge initially correspond to the expected elastic value of −0.30 and transition to the plastic value of −0.50. This is true for any points that undergo a uniaxial type of deformation. The ratios produced at the fracture point are clearly different from those of the uniaxial elongation generated at the hole periphery.

Figure 6A:
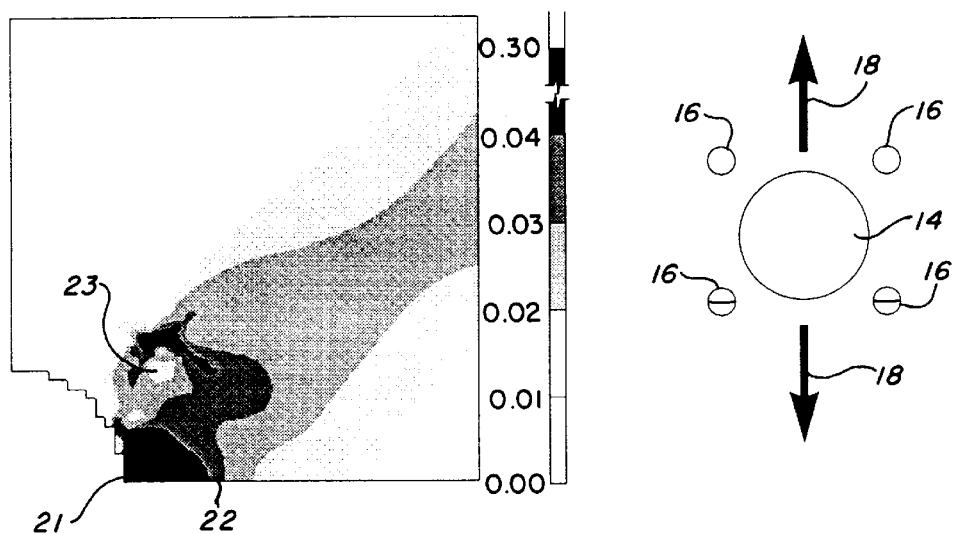
FIG. 6a shows a predicted equivalent plastic strain in a tension specimen with hole and reduced thickness ratio of 0.25 at 45 degrees (FIG. 2d).
Figure 6B:
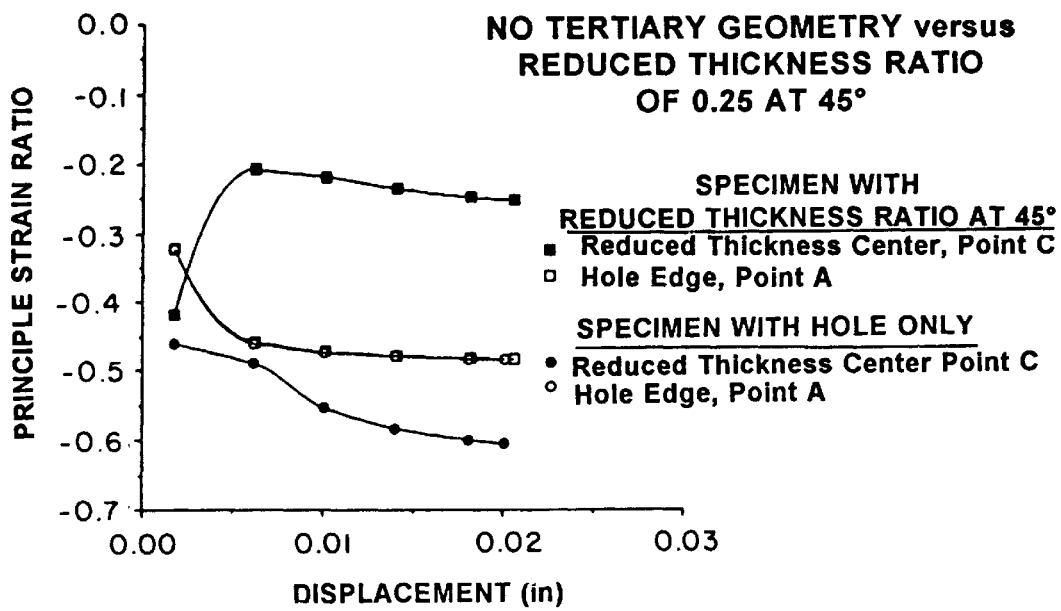
FIG. 6b shows a predicted principal strain ratio history for a specimen in tension with a hole and reduced thickness ratio of 0.25 at 45, 135, 225 and 315 degrees (FIG. 2d) compared with a specimen with no tertiary geometry (FIG. 2b).
Figure 6C:
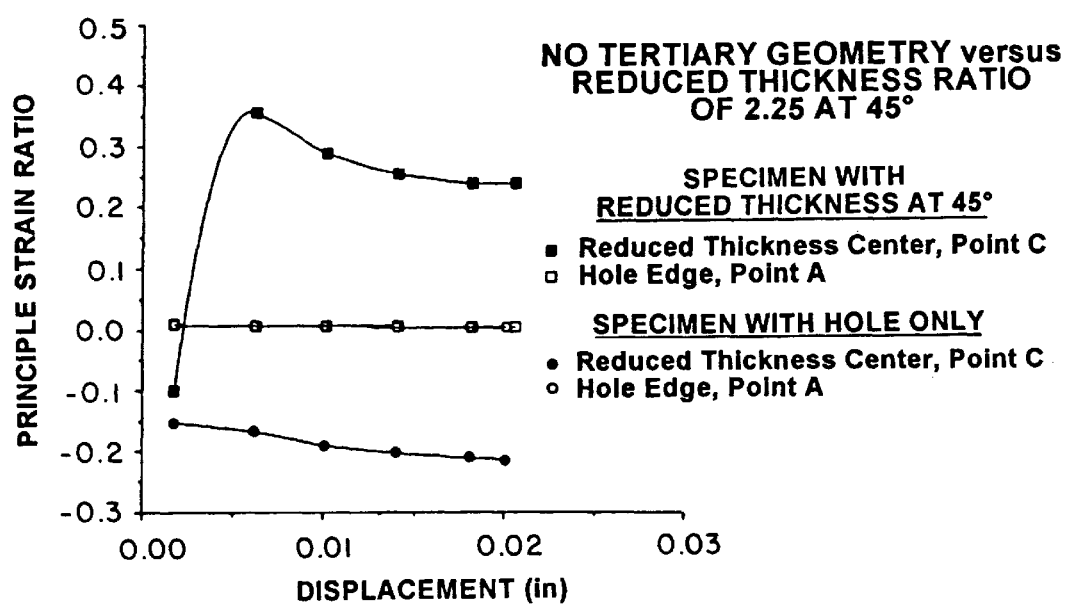
FIG. 6c shows a predicted principal stress ratio history for a specimen in tension with a hole and reduced thickness ratio of 0.25 at 45, 135, 225 and 315 degrees (FIG. 2d) compared with a specimen with no tertiary geometry (FIG. 2b).

To demonstrate fracture initiation site control, a tertiary specimen 40 was produced having 045-135-225-315 reduced section 16 locations. A thickness ratio of 0.25 was used to increase the magnitudes of strains and stresses at the reduced thickness 16 locations. The experimental results, as shown in FIGS. 6a–c, for the specimen showed successful initiation of fracture in the reduced thickness 16 sections at 225 and 315 degrees. The finite element prediction of the equivalent plastic strain field for the fourth specimen 40 is shown in FIG. 6a. Comparison of strain and stress ratios at Point 21 of the hole boundary and the reduced sections described by Point 23 shows principal strain ratios of −0.25 and −0.50 (FIG. 6b), respectively, and principal stress ratios of 0.00 and 0.25 (FIG. 6c), respectively. The ratios at the fracture initiation sites are very different from those at the 000–180 degree hole edge positions.

Figure 7:
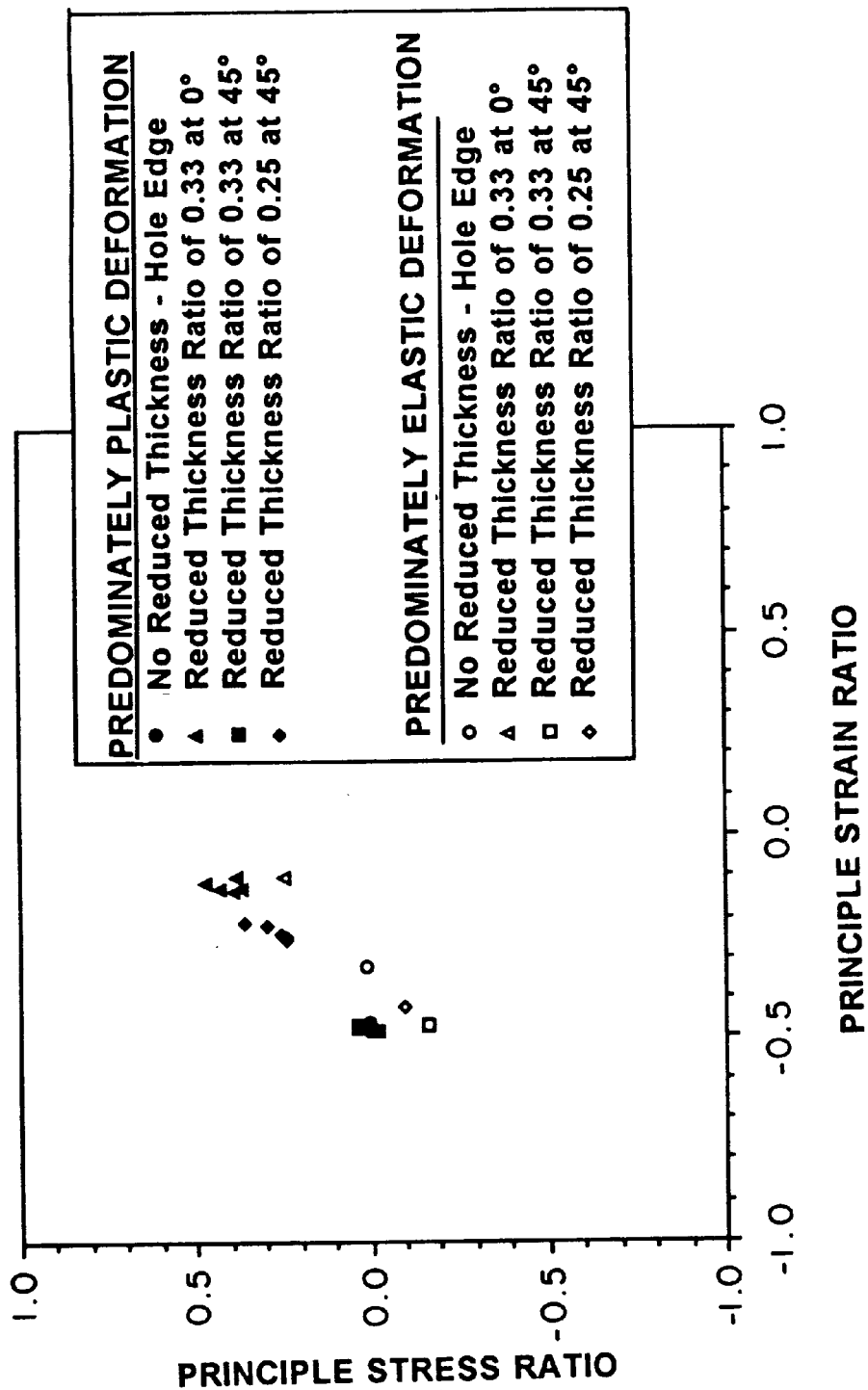
FIG. 7 shows a range of strain ratio versus stress ratio histories produced during deformation of specimen for hole edge and reduced thickness areas of 0.33 at hole edge at 0 and 180 degrees, reduced thickness ratio of 0.33 at 45, 135, 225 and 315 degrees, and reduced thickness ratio of 0.25 at 45, 135, 225 and 315 degrees.

The principal stress ratios are plotted against principal strain ratios for all sites of first fracture initiation for the four specimens (FIG. 7). FIG. 7 clearly shows the range of ratio values produced by the specimens. The data points are separated into responses from predominately elastic responses, shown by the open symbols, and those in the predominately plastic response region, shown in closed symbols. The elastic strain ratios range from −0.50 to −0.10 while the stress ratios range from −0.20 to 0.30. The plastic strain ratios range from −0.50 to −0.10 while the stress ratios range from 0.00 to 0.50. The direction of the evolution from predominately elastic to plastic regimes varies for the different specimens. All elastic regime values lie in a band, as do the plastic regime values. This is related to the plane stress character of the specimens.

In summation, simple material test specimen designs have been demonstrated that generate multiaxial strain states leading to fracture using standard tension testing machines well known to those practicing the art. The basic specimen design for the test was a sheet with a circular hole and additional reduced thickness 16 areas near the circular hole. It was demonstrated using an Al 2024 sheet material in the T3 condition. The fracture initiation sites were effectively moved from the hole boundary to two different reduced thickness 16 areas at 0 and 45 degree orientations. Strain ratio histories were determined by finite element analysis of the specimen. In-plane multiaxial plastic strain ratios, ranging from −0.50 to −0.10, were generated by these specimens. The results of these simple demonstration specimens also provided the basis for further increasing the number of data points obtained per specimen, sampling larger ranges of strain states to fracture initiation and the possibility of generating and tracking nonproportional histories by a simple test method on standard test machines.

The use of alternative methods of invention fabrication depends on the material to be tested. Materials such as metallic sheet or ingots are amenable to the machining processes described above. Casting methods for metals, hot isostatic pressing for powdered metallurgy, and injection molding for polymers are three examples of alternative fabrication methods suited to additional types of materials.

The secondary and tertiary geometric features may be tailored for better efficiency in generating desired, predetermined stress states. For example, the secondary may be shaped more like an ellipse, a notch, or a cross. The tertiary features may take on a similar range of shapes. Through the use of computer models it has been determined that ellipsoidal-shaped dimples produce a wider range of stress states than the simple spherical dimples.

It is possible to use similar specimen designs to determine the anisotropic yield surface instead of the fracture surface. This improvement is of benefit in sheet metal forming operations such as stamping, drawing, and stretching.

Although the invention has been described in relation to an exemplary embodiment thereof, it will be understood by those skilled in the art that still other variations and modifications can be affected in these preferred embodiments without detracting from the scope and spirit of the invention as described in the claims.

What is claimed is:

1. An apparatus for determination of critical strain and stress states for multiaxial fracture, comprised of:

a test specimen whose critical strain and stress states for multiaxial fracture is to be determined having a geometry that will generate a global deformation field;

a test fixture capable of deforming the test specimen under tension in a controlled fashion;

means for monitoring the deformation of the test specimen to identify when and where a fracture occurs;

means for recording data relating to the force versus extension response of the specimen;

means for developing a constitutive model and constitutive parameters by existing standard methods for the material;

means for performing a stress analysis on the data by analytical or computational simulation to recreate stress and strain histories throughout the specimen; and means for correlating the data of the monitoring means and the means for performing the stress analysis to establish fracture limits.

2. An apparatus, as in claim 1, where the means for developing a constitutive model and constitutive parameters by existing standard methods for the material; means for performing a stress analysis on the data by analytical or computational simulation to recreate stress and strain histories throughout the specimen; and means for correlating the data of the monitoring means and the means for performing the stress analysis to establish fracture limits, is a computer.

3. A method for determining the critical strain and stress states for multiaxial fracture of a material, comprising the steps of:

selecting a test specimen of a geometry which when subjected to global deformation generates a desired multi-axial strain and stress states leading to multiaxial fracture;

deforming the test specimen under tension with a test fixture in a controlled fashion;

monitoring the deformation of the test specimen to identify when and where a fracture occurs;

recording data relating to the force versus extension response of the specimen;

selecting a constitutive model and constitutive parameters for the material being tested in the specimen;

performing a stress analysis on the specimen by analytical or computational simulation to calculate the stress and strain histories throughout the specimen; and correlating the data of the monitoring means and the means for performing the stress analysis to establish fracture limits.

* * * * *

UNITED STATES PATENT AND TRADEMARK OFFICE
CERTIFICATE OF CORRECTION

PATENT NO. : 5,905,204
DATED : May 18, 1999
INVENTOR(S) : DeGiorgi, et al

It is certified that error appears in the above-indentified patent and that said Letters Patent is hereby corrected as shown below:

Title page,

Delete [75] Inventors: Virginia G. DeGiorgi, Nanjemoy, Md.;
Andrew B. Geltwalter, Alexandria, Va.

Insert: Page 1, Col. 1, Line 5:
[75] Inventors: Virginia G. DeGiorgi, Nanjemoy, Md.;
Andrew B. Geltwalter, Peter Matic,
Richard K. Everett. all of Alexandria, Va.

Signed and Sealed this

Twelfth Day of October, 1999

Q. TODD DICKINSON

*Attest:*

*Attesting Officer*     *Acting Commissioner of Patents and Trademarks*